(12) United States Patent
Vause et al.

(10) Patent No.: US 10,208,925 B2
(45) Date of Patent: Feb. 19, 2019

(54) SOFT CONFORMAL LAPAROSCOPIC INSTRUMENT

(71) Applicant: Soft Robotics, Inc., Cambridge, MA (US)

(72) Inventors: Carl Everett Vause, Concord, MA (US); Joshua Aaron Lessing, Cambridge, MA (US); Ryan Richard Knopf, Cambridge, MA (US)

(73) Assignee: Soft Robotics, Inc., Cambridge, MA (US)

( * ) Notice: Subject to any disclaimer, the term of this patent is extended or adjusted under 35 U.S.C. 154(b) by 114 days.

(21) Appl. No.: 14/645,301

(22) Filed: Mar. 11, 2015

(65) Prior Publication Data
US 2015/0257839 A1    Sep. 17, 2015

Related U.S. Application Data (60) Provisional application No. 61/950,954, filed on Mar. 11, 2014.

(51) Int. Cl.
*A61B 17/22* (2006.01)
*F21V 14/08* (2006.01)
(Continued)

(52) U.S. Cl.
CPC .......... *F21V 14/085* (2013.01); *A61B 17/221* (2013.01); *A61B 17/22032* (2013.01);
(Continued)

(58) Field of Classification Search
CPC ............... F21V 33/0076; F21V 14/085; F21V 23/0414; A61B 34/30; A61B 17/29; A61B 17/221; A61B 17/22031; A61B 17/22032; A61B 17/22034; A61B 17/22035; A61B 2017/2902; A61B 2017/2906; A61B 2017/2926; A61B 2017/2927; A61B 2017/2945; A61B 2017/22051; A61B 2017/22054; A61B 2017/22055;
(Continued)

(56) References Cited

U.S. PATENT DOCUMENTS 4,708,140 A * 11/1987 Baron .................... A61B 17/12
  606/158
5,019,042 A * 5/1991 Sahota .............. A61M 25/1002
  604/101.01
(Continued)

FOREIGN PATENT DOCUMENTS

| WO | 20120148472 A2 | 11/2012 |
| WO | 2013110086 A1 | 7/2013 |
| WO | 20140196928 A1 | 12/2014 |

OTHER PUBLICATIONS

International Search Report dated Jun. 10, 2015 for International Application No. PCT/US2015/020030 filed Mar. 11, 2015 (6 sheets).

*Primary Examiner* — Jocelin Tanner (57) ABSTRACT

A soft robotic instrument that is capable of changing its form factor (e.g., expanding and contracting) during use to facilitate minimally invasive surgery. The instrument may be formed wholly or partly of an elastomeric, electrically insulating material for mitigating the risk of injuring tissue and for mitigating the risk of electrical arcing during electrosurgery.

19 Claims, 5 Drawing Sheets

(51) Int. Cl.
  *B25J 15/00* (2006.01)
  *B25J 15/12* (2006.01)
  *A61B 17/221* (2006.01)
  *A61B 17/29* (2006.01)
  *F21L 4/00* (2006.01)
  *F21V 23/04* (2006.01)
  *A61B 34/30* (2016.01)
  *A61B 17/00* (2006.01)
  *A61B 17/30* (2006.01)
  *A61B 90/00* (2016.01)

(52) U.S. Cl.
  CPC .............. *A61B 17/29* (2013.01); *A61B 34/30* (2016.02); *B25J 15/0023* (2013.01); *B25J 15/12* (2013.01); *F21L 4/00* (2013.01); *F21V 23/0414* (2013.01); *A61B 2017/00535* (2013.01); *A61B 2017/00539* (2013.01); *A61B 2017/00557* (2013.01); *A61B 2017/2215* (2013.01); *A61B 2017/2217* (2013.01); *A61B 2017/306* (2013.01); *A61B 2090/0427* (2016.02); *A61B 2090/0817* (2016.02)

(58) Field of Classification Search
  CPC ........... A61B 2017/22062; A61B 2017/22064; A61B 2017/22071; A61B 2017/2217; A61B 2017/00539; A61B 2017/2215; A61B 2017/306; A61B 2017/0057; A61B 2017/00535; A61B 2017/003; A61B 2090/0817; A61B 2090/0427; F21L 4/00; B25J 15/0023; B25J 15/12
  See application file for complete search history.

(56) References Cited

U.S. PATENT DOCUMENTS

| | | | |
|---|---|---|---|
| 5,236,437 A * | 8/1993 | Wilk | A61B 17/22032 604/908 |
| 5,400,773 A * | 3/1995 | Zhu | A61B 17/0218 600/205 |
| 6,036,706 A * | 3/2000 | Morejohn | A61B 17/122 606/157 |
| 6,187,013 B1 * | 2/2001 | Stoltze | A61F 2/958 606/108 |
| 2002/0049408 A1 * | 4/2002 | Van Moorlegem | A61M 25/1027 604/101.01 |
| 2005/0267492 A1 * | 12/2005 | Poncet | A61B 17/221 606/114 |
| 2006/0282111 A1 * | 12/2006 | Morsi | A61B 17/22032 606/194 |
| 2007/0129749 A1 * | 6/2007 | Thomas | A61M 25/10 606/194 |
| 2008/0167678 A1 * | 7/2008 | Morsi | A61B 17/320725 606/200 |
| 2010/0263500 A1 | 10/2010 | Bannasch et al. | |

* cited by examiner

SOFT CONFORMAL LAPAROSCOPIC INSTRUMENT

CROSS-REFERENCE TO RELATED APPLICATIONS

This application claims the benefit of priority under 35 U.S.C. § 119(e) to U.S. Provisional Patent Application No. 61/950,954 by Carl Everett Vause, et al. titled "Soft Conformal Laparoscopic Instrument." The entire disclosure of the foregoing application is incorporated herein by reference for all purposes.

FIELD OF THE DISCLOSURE

The disclosure relates generally to the field of medical devices and more particularly to soft robotic instruments for performing medical procedures.

BACKGROUND OF THE DISCLOSURE

Laparoscopic surgery is a surgical technique in which operations in the abdomen are performed through small incisions (usually 0.5-1.5 cm). There are a number of advantages provided to a patient undergoing laparoscopic surgery versus an open surgical procedure. These include a much smaller incision, reduced pain and hemorrhaging, and shorter recovery time.

Modern laparoscopic instruments, including robotically-assisted laparoscopic instruments, typically include an elongated shaft that terminates in a mechanical end effector for reaching into a patient's body and manipulating the patient's tissue in a desired manner. The end effector may be a simple mono-polar electrode, a toothed grasper, scissors, or some other device or structure that is adapted to perform a desired function during a laparoscopic procedure. Laparoscopic instruments are generally formed of rigid materials, such as metals and plastics, in order to facilitate articulation, grasping, cutting, and other movements and/or actions that may be necessary.

Conventional laparoscopic instruments are associated with a number of shortcomings. For example, due to their rigidity, and since they are generally not conformal and are not capable of significantly altering their shape during use, such instruments have outer dimensions that define minimum and maximum dimensions of surgical access ports in patients' through which they extend. This restricts the number of useful procedures and operating environments in which such instruments may be employed.

A further shortcoming associated with conventional laparoscopic instruments is that, since these instruments often include teeth, blades, jaws, serrations, or other such features that are formed of hard plastic and/or metal, there exists a significant risk of unintentionally injuring tissue while performing a laparoscopic procedure, such as may result from accidental and/or overly-forcible contact with tissue.

A further shortcoming associated with conventional laparoscopic instruments is that, in embodiments of such instruments that have metallic surfaces and that are used for performing electosurgery and/or are used in conjunction with other instruments that are used for electrosurgery, instances of electrical arching have been known to occur, sometimes resulting in injury to patients.

The above described challenges have heretofore been mitigated by heightened surgeon awareness, extensive training, and complete avoidance of certain anatomical structures and pathologies that are known to present challenges. This places a significant burden on surgeons and limits the range of applications in which laparoscopic instruments may be used.

BRIEF DESCRIPTION OF THE DRAWINGS

FIG. 1c is a cross sectional view illustrating a shaft cuff of the soft robotic instrument shown in FIG. 1a.

SUMMARY OF THE INVENTION

"Soft robotic" actuators that are configured to perform new fundamental motions—such as bending, twisting, and straightening—are described. Soft robotic technologies are discussed in PCT International Publication Number WO2012/148472, which is incorporated herein by reference in its entirety. The present invention includes the implementation of soft robotic technologies into specific configurations that are useful for minimally invasive surgical techniques, and minimally invasive surgical methods that employ such soft robotic configurations.

Certain embodiments of the present disclosure describe fabrication and operation of pressurizable networks of channels or chambers (Pneu-Nets) embedded in elastomeric or extensible bodies. The pressurizable network actuators can be programmed to change shape and mechanical properties using an external stimulus, including pneumatic or hydraulic pressure. The soft robot structures utilize designs of embedded pneumatic or hydraulic networks of channels in elastomers that inflate like balloons for actuation or in folded extensible fabrics that can open up when pressurized. A plurality of chambers embedded within an elastomer can be used as a series of repeating components. Stacking and connecting these repeated components provide structures capable of complex motion. In this type of design, complex motion requires only a single pressure source (although more than one source can be used, if desired). The appropriate distribution, configuration, and size of the pressurizable networks, in combination with a sequence of actuation of specific network elements, determine the resulting movement.

In one aspect, the present invention relates to a medical device that includes a soft robotic actuator (referred to, for brevity, as an "actuator") comprising an elastomeric material and a plurality of interconnected fluid compartments. The actuator is moveable between first and second configurations characterized by different first and second internal pressures within the plurality of fluid compartments, respectively. The device also includes a fluid conduit sized and shaped to couple to a fluid source, which conduit is in fluid communication with at least one of the fluid compartments so as to transmit fluid pressure between the fluid source and the fluid compartment(s). The medical device can optionally include one or more additional features. For instance, the actuator can include a strain limiting portion about which the actuator bends when moved between the first and second configurations. Alternatively or additionally, the second configuration can be characterized by a larger outer diameter than the first configuration, and the outer diameter of the first configuration can be less than the inner diameter of a medical device (such as a dilator, an introducer sheath, and a working channel of a laparoscope or endoscope) through which the medical device is inserted into a patient. When it is moved from the first to the second configuration, the actuator optionally undergoes a motion such as bending, twisting, curling and straightening. In some cases, the device includes a plurality of actuators defining a grasping structure, in which case the grasping structure may be open when the actuators are in a first configuration and closed when the actuators are in the second configuration, or vice versa. The grasping structure may also include a mesh, a membrane or a polymer sheet extending between the plurality of actuators, such that the grasping structure defines a cup. In some cases, the device includes first and second loop shaped actuators which define a substantially spherical space. To do this, the second actuator is attached to the first actuator but is oriented transversely to it. Additionally, the device optionally includes a user-activated mechanism for moving fluid between the fluid reservoir and the plurality of fluid chambers.

In another aspect, the present invention relates to a system for treating a patient that includes a medical device comprising an actuator and a fluid conduit substantially as described above, along with a fluid source configured to couple to the fluid conduit and a user-activated mechanism (also as described above) for moving fluid between the fluid source and the plurality of fluid compartments, thereby changing the configuration of the actuator. The system preferably (though not necessarily) includes a hollow shaft, in which case the actuator is slidably disposed within the hollow shaft. As discussed above, the system can also include a plurality of actuators defining a grasping structure, in which case the grasping structure may be open when the actuators are in a first configuration and closed when the actuators are in the second configuration, or vice versa. The grasping structure may also include a mesh, a membrane or a polymer sheet extending between the plurality of actuators, such that the grasping structure defines a cup. Alternatively, the system includes first and second loop shaped actuators which define a substantially spherical space. As above, this is accomplished by means of the attachment and transverse orientation of the second actuator relative to the first actuator. The method also optionally includes In another aspect, the present invention relates to a method of treating a patient which includes inserting at least part of a medical device or system comprising a soft robotic actuator and fluid source, as described above, into the body of a patient. The method can also include moving the actuator from the first to the second configuration, which step may entail contacting a body tissue and/or a medical instrument with the actuator. Alternatively or additionally, the step of moving the actuator includes one or more of pushing, pulling or grasping a body tissue without damaging the tissue. As is discussed in greater detail below, one advantage of the soft robotic actuators relative to currently used rigid medical devices is that the soft robotic actuators may be significantly less traumatic, facilitating the atraumatic or minimally-traumatic manipulation of delicate body tissues. In some cases, the insertion of the device into the body includes disposing a distal end of a hollow shaft (e.g. a catheter, cannula, dilator, laparoscope or endoscope working channel) within the body of the patient and advancing at least a portion of the medical device through the hollow shaft and into the body of the patient.

In still another aspect, a soft body robotic device includes a flexible molded body having a plurality of interconnected chambers disposed within the molded body. A portion of the molded body is comprised of an elastically extensible material and a portion of the molded body is strain limiting relative to the elastically extensible material. The thickness of the molded body is at least 1 mm. The soft body robotic device further includes a pressurizing inlet that is configured to receive fluid for the plurality of interconnected chambers. The molded body in the soft body robotic device is configured to preferentially expand when the plurality of interconnected chambers are pressurized by the fluid, causing a bending motion around the strain limiting portion of the molded body.

And in another aspect, a soft body robotic device includes a flexible molded body comprising a plurality of interconnected pleated chambers. The flexible molded body includes a flexible material and is affixed to a strain limiting member in such a manner that the strain limiting member forms a wall of the plurality of interconnected pleated chambers. The thickness of the molded body is at least 1 mm. The soft body robotic device further includes a pressurizing inlet that is configured to receive fluid for the plurality of interconnected pleated chamber. The plurality of interconnected pleated chambers are configured to preferentially unfold when the flexible molded body is pressurized through the pressurizing inlet, causing bending motion around the strain limiting member.

In yet another aspect, a soft body robotic device is capable of extension. This soft robotic device includes a flexible molded body having a plurality of interconnected chambers disposed within the molded body. The soft robotic device also includes a sealing member in a facing relationship with the flexible molded body, in which the flexible molded body and the sealing member together define a plurality of channels. Each channel is defined by upper, lower and side walls. The sealing member is in a state of compression in its resting state. The soft robotic device additionally includes a pressurizing inlet in fluid communication with the plurality of channels. The plurality of channels are positioned and arranged such that the soft body robotic device expands to relieve the strain in the sealing member when the soft body robotic device is pressurized through the inlet.

DETAILED DESCRIPTION OF THE PREFERRED EMBODIMENTS

The present invention will now be described more fully hereinafter with reference to the accompanying drawings, in which preferred embodiments of the invention are shown. The invention, however, may be embodied in many different forms and should not be construed as being limited to the embodiments set forth herein. Rather, these embodiments are provided so that this disclosure will be thorough and complete, and will fully convey the scope of the invention to those skilled in the art. In the drawings, like numbers refer to like elements throughout.

In accordance with the present disclosure, a soft robotic instrument is provided that is capable of changing its form factor (e.g., expanding and contracting) during use to facilitate minimally invasive surgery. Although the present invention is described with specific reference to laparoscopic surgical techniques, it is to be appreciated that the present invention may be equally applicable to other types of minimally invasive surgery. The instrument may be formed wholly or partly of an elastomeric, electrically insulating material for mitigating the risk of injuring tissue and for mitigating the risk of electrical arcing during electrosurgery.

Figure 1A:
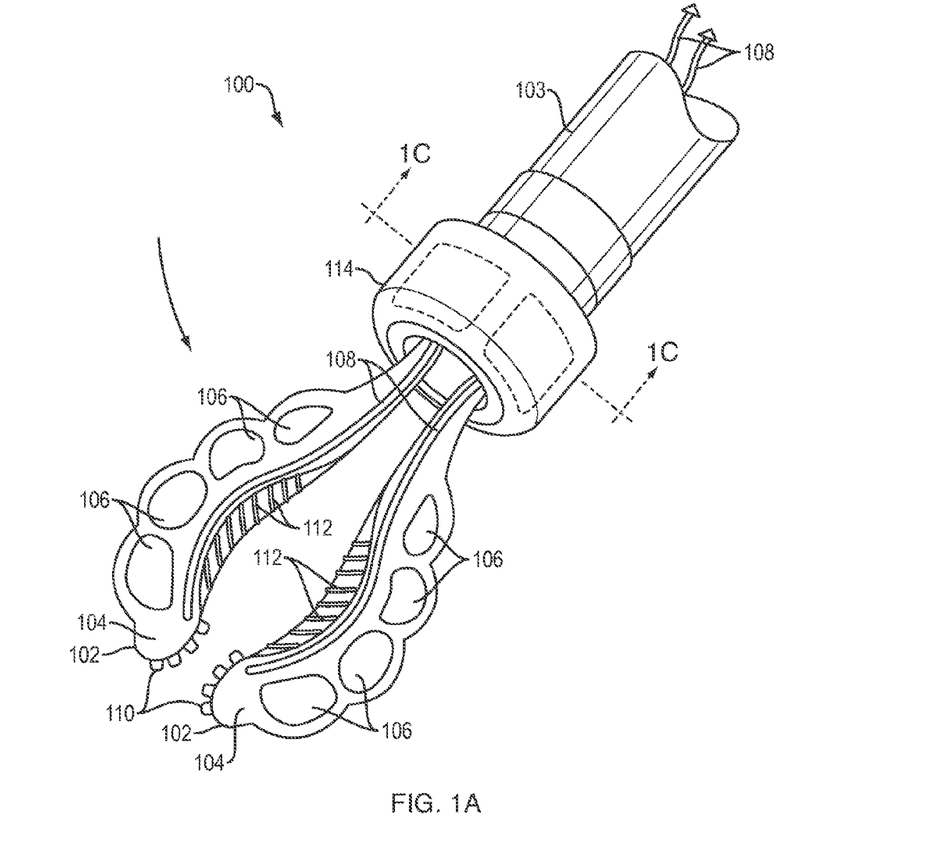
FIG. 1a is perspective view illustrating a first exemplary embodiment of a soft robotic instrument in accordance with the present disclosure.

Referring to FIG. 1a, a first embodiment of an instrument in accordance with the present disclosure includes a grasping device 100 (hereinafter "the grasper 100") that employs soft robotic actuators 102 in place of metal jaws that are typically employed by conventional laparoscopic graspers. The actuators 102 may extend from an opening in an elongated, tubular shaft 103 that may be inserted into the body of a patient during a laparoscopic procedure as further described below.

Each of the actuators 102 may be defined by a flexible body 104 having one or more pressurizeable (e.g., inflatable) fluid channels and/or chambers 106 formed therein. A portion of the flexible body 104 may be formed of an elastomeric material and another portion of the flexible body 104 may be strain limiting relative to the elastomeric material. The elastomeric portions of the flexible body 104 may be caused to bend around the strain limiting portions via pressurization and depressurization of the fluid chambers 106, thereby allowing the actuators 102 to be controllably expanded, contracted, shaped, and/or moved in a predefined manner.

Figure 1B:
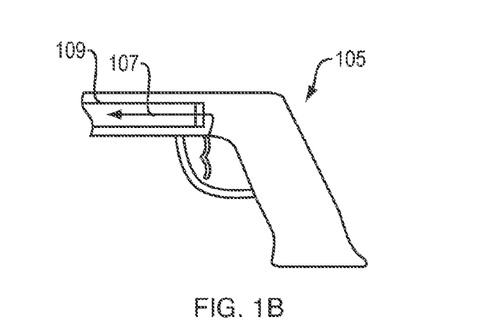
FIG. 1b is a side view illustrating an exemplary embodiment of pressurizeable fluid source in accordance with the present disclosure.

The fluid chambers 106 may be connected to one or more pressurizeable fluid sources 105 (see FIG. 1b), such as via fluid conduits (not shown) that extend through the shaft 103. The pressurizeable fluid source 105 may be manually or automatically operated to pressurize and depressurize the fluid chambers 106 in the actuators 102. Referring to FIG. 1b, a non-limiting example of the pressurizeable fluid source 105 may include a trigger-operated pump or piston 107 that drives an amount of working fluid through a cylinder 109 that is coupled to the fluid conduits in the shaft 103. Alternatively, the pressurizeable fluid source 105 may be embodied by any suitable pneumatic or hydraulic fluid pressurization device, including, but not limited to, hand pumps, electric compressors, pressurized gas canisters, etc.

Each of the actuators 102 may be provided with a corresponding rigid wire 108 (e.g., Nitinol wire) embedded therein that may extend through the shaft 103. A portion of the wires 18 may protrude from a butt end of the shaft 103 and may be manually or automatically manipulated to deploy and retract the actuators 102 relative to the tip of the shaft 103. For example, when the grasper 100 is used to perform a laparoscopic procedure, the actuators 102 may be depressurized (e.g., deflated) and, having a reduced size relative to the pressurized configuration of the actuators 102 shown in FIG. 1a, may be fully retracted into the hollow interior of the shaft 103. The shaft 103 may then be inserted into a surgical access port in a patient. Once the tip of the shaft 103 is appropriately positioned within the patient, the wires 108 may be manipulated (e.g., pushed) to extend the depressurized actuators 102 out of the tip of the shaft 103 and into a suitable position within the patient, such as surrounding a portion of tissue that is to be grasped. The pressurizeable fluid source 105 may then be actuated to pressurize the actuators 102, causing the actuators 102 to expand, bend, and/or move to grasp the desired tissue. The grasper 100 may then be used to manipulate the grasped tissue in a desired manner.

When the grasper 100 is to be removed from the patient, the actuators 102 may be depressurized and the wires 108 may be manipulated (e.g., pulled) to retract the actuators 102 back into the shaft 103. The shaft 103 may then be withdrawn from the surgical access port. It will therefore be appreciated that the surgical access port need only be as large as is necessary to facilitate insertion and removal of the shaft 103, and need not be so large as to accommodate the actuators 102 in their expanded (i.e., pressurized), working configuration shown in FIG. 1a. Moreover, since the actuators 102 are formed of a relatively soft, elastomeric material, the risk of unintentionally damaging tissue within the patient is mitigated relative to conventional laparoscopic grabbers that are formed of rigid materials such as metal and plastic. Still further, since the elastomeric material of the actuators 102 is electrically insulating, the risk of electrical arcing during electrosurgery is mitigated relative to laparoscopic grabbers that have metallic components and/or surfaces.

In addition to the rigid wires 108, it is contemplated that the actuators 102 may be provided with various other embedded, rigid components to aid in the actuation, deployment, and/or retraction of the actuators 102. The actuators 102 may further be provided with rigid exterior features, including, but not limited to, teeth 110 and blades 112, such as may be formed of metal or plastic, for aiding in the grasping and/or cutting of tissue. Such rigid elements could be adapted for controllable actuation, such as through the introduction of variable fluid pressure, as well as via mechanical and/or electrical activation. It is further contemplated that the actuators 102 can be provided with embedded electrodes for performing mono-polar or bi-polar electrosurgical techniques, such as electro-cautery. Still further, it is contemplated that the actuators 102 may be provided with embedded transducers for performing ultrasound or Doppler imaging. Still further, while the grasper 100 has been described and shown as having two actuators 102, it is contemplated that the grasper 100 may be provided with an additional number of similar actuators, such as may be suitable or advantageous for manipulating various types of tissue or organs. Still further, it is contemplated that the actuators 102 may be provided with internal fluid conduits and outlet ports for conveying and expelling liquid onto targeted tissue (e.g., to perform irrigation). Still further, it is contemplated that the actuators 102 may be provided with internal compartments or channels for holding and controllably deploying surgical instruments, such as biopsy needles or laser fibers.

Figure 1C:
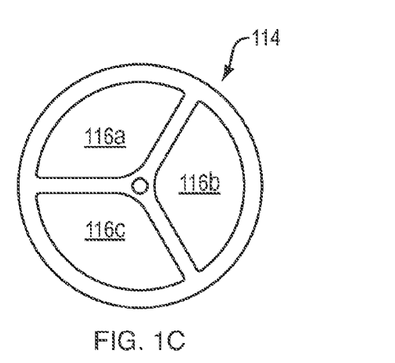

Referring to FIGS. 1a and 1c, the grasper 100 may be provided with an elastic cuff 114 that may fit over the tip of the shaft 103. The cuff 114 may be provided with a plurality of internal fluid chambers 116a-c that may each be connected to an independent, pressurizeable fluid source (not shown) that may be similar to the pressurizeable fluid source 105 described above. By selectively pressurizing and depressurizing one or more of the compartments 116a-c, the actuators 102 may be controllably oriented (e.g., angled or otherwise displaced) relative to the shaft 103.

Figure 2A:
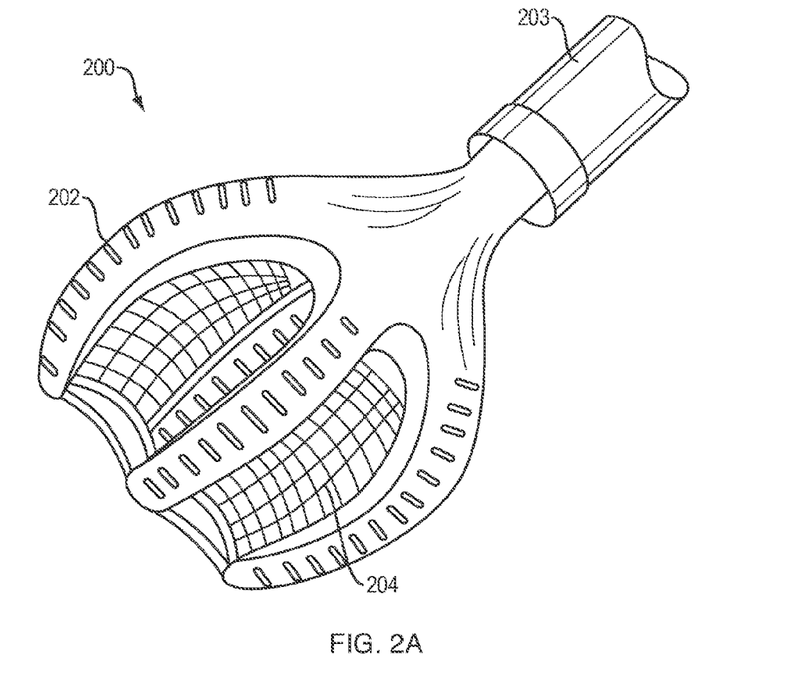
FIG. 2a is perspective view illustrating a second exemplary embodiment of a soft robotic instrument in accordance with the present disclosure in a pressurized configuration.
Figure 2B:
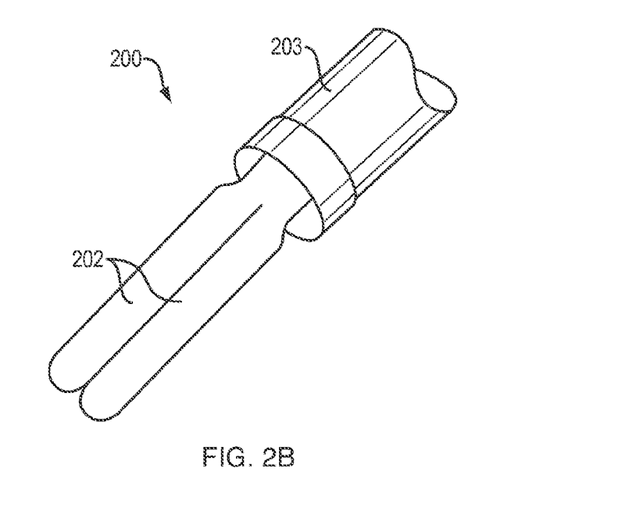
FIG. 2b is perspective view illustrating the soft robotic instrument shown in FIG. 2a in a depressurized configuration.

Referring to FIGS. 2a and 2b, an exemplary embodiment of a "multi-fingered" grasper 200 in accordance with en embodiment of the present disclosure is shown. The grasper 200 may be similar to the grasper 100 described above, but may be provided with four actuators 202 having internal fluid compartments that are connected to a common pressurizeable fluid source that is similar to the pressurizeable fluid source 105 described above. A lightweight meshing 204 may extend between each adjacent pair of actuators 202 so that grasper 200 may, in its pressurized configuration shown in FIG. 2a, form a "cup" that defines an interior volume. The cup may be placed over a body of tissue that is to be removed or otherwise manipulated. Of course, it is contemplated that the actuators 202 may be configured to form various types of enclosures other than a round cup, such as a tent or a box. Moreover, as described above in relation to the grasper 100, the grasper 200 may be provided with various rigid features, irrigation fluid conduits, and/or other embedded structures and devices.

Referring to FIG. 2b, the grasper 200 is shown in a depressurized configuration. As can be seen, all of the actuators 202 are collapsed into a single, longitudinally extending "finger" having a diameter that is smaller than, or substantially equal to, the diameter of the shaft 203 from which the actuators 202 extend. The meshing 204 may be collapsed within the actuators 202 in a folded/interleaved configuration. Thus, like the grasper 100, the grasper 200 may, in its depressurized configuration, be inserted into, and withdrawn from, a surgical access port in a patient that is only large enough to accommodate the shaft 203.

Figure 3A:
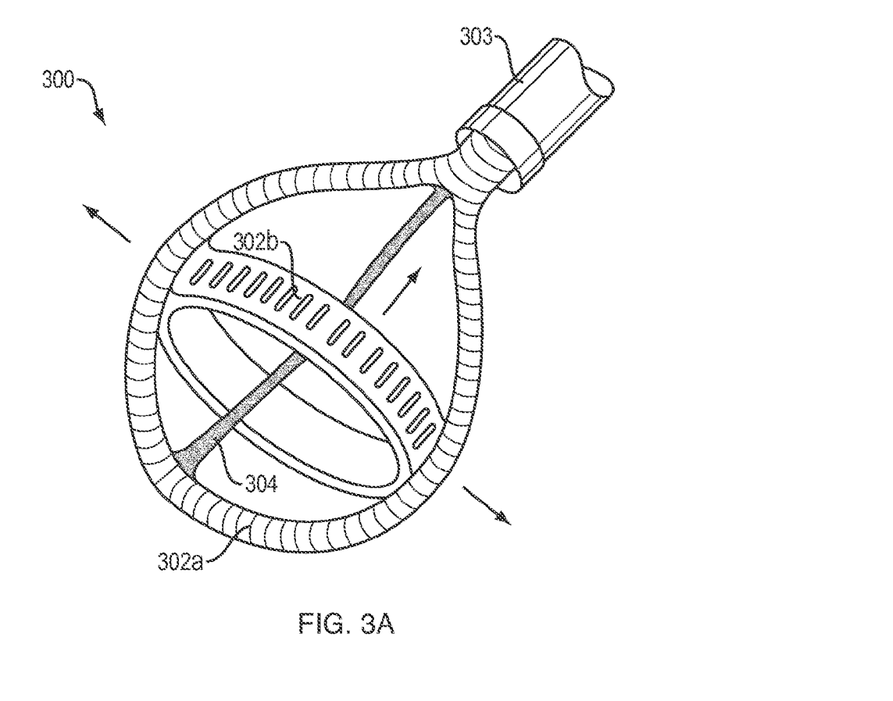
FIG. 3a is perspective view illustrating a third exemplary embodiment of a soft robotic instrument in accordance with the present disclosure in a pressurized configuration.

In addition to the graspers 100 and 200 described above, it is contemplated that a soft robotic laparoscopic instrument in accordance with the present disclosure may be implemented using a variety of other configurations for addressing various operating needs. For example, referring to FIGS. 3a and 3b, the instrument may be embodied by a displacer 300 that may include a pair of longitudinally and laterally oriented loop-shaped actuators 302a, 302b that are connected to one another in a transverse relationship to define a substantially spherical volume. The actuators 302a, 302b may have internal fluid compartments that are connected to a common pressurizeable fluid source (not shown) that is similar to the pressurizeable fluid source 105 described above. A wire or tendon 304 may extend longitudinally from the shaft 303 and may be connected to a distal terminus of the longitudinally-extending actuator 302a. After the actuators 302a, 302b of the displacer 300 are pressurized as shown in FIG. 3a, the tendon 304 may be pulled longitudinally into the shaft 303 (as indicated by the longitudinally oriented arrow in FIG. 3a) to radially expand the displacer 300 (as indicated by the laterally oriented arrows in FIG. 3a). The pressurized displacer 300 may thereafter be used to displace sensitive tissues (lung, liver, etc.) to provide convenient access to adjacent areas.

Figure 3B:
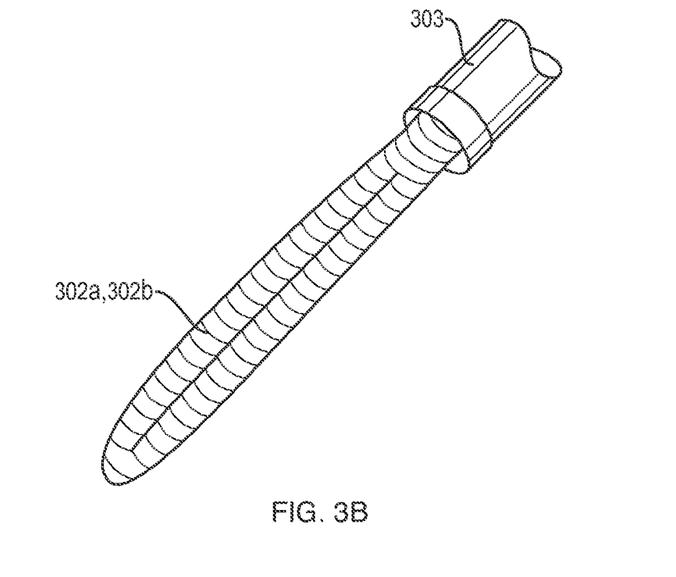
FIG. 3b is perspective view illustrating the soft robotic instrument shown in FIG. 3a in a depressurized configuration.

Referring to FIG. 3b, the displacer 300 is shown in a depressurized configuration. As can be seen, the actuators 302 are collapsed into a single, longitudinally extending "finger" having a diameter that is smaller than, or substantially equal to, the diameter of the shaft 303 from which the actuators 302 extend. Thus, like the graspers 100 and 200 described above, the displacer 300 may, in its depressurized configuration, be inserted into, and withdrawn from, a surgical access port in a patient that is only large enough to accommodate the shaft 303.

Figure 4:
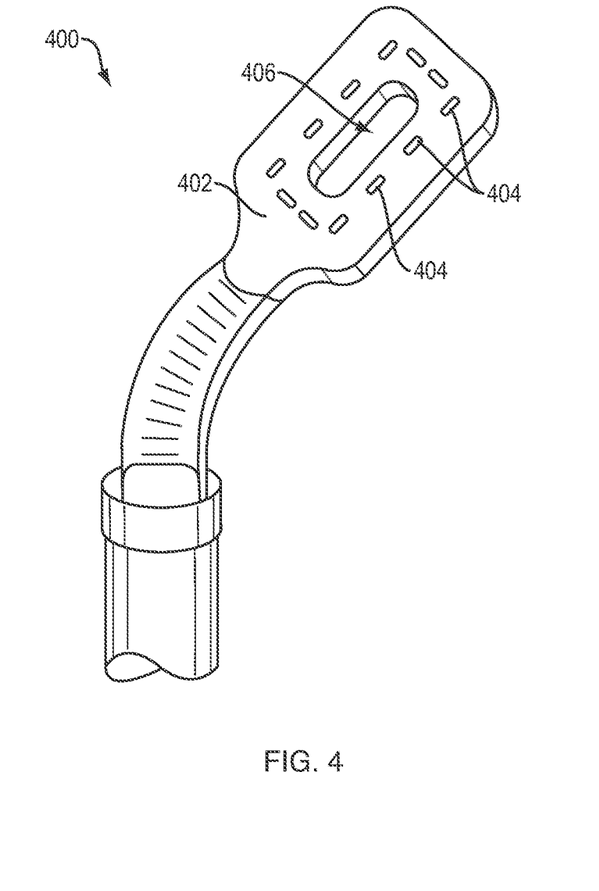
FIG. 4 is perspective view illustrating a fourth exemplary embodiment of a soft robotic instrument in accordance with the present disclosure.

Referring to FIG. 4, another soft robotic laparoscopic instrument in accordance with the present disclosure may be embodied by a spade 400 that may be used to displace or otherwise manipulate tissue within a patient. The spade 400 may include a single actuator 402 that may have an internal fluid compartment that is connected to a pressurizeable fluid source (not shown) that is similar to the pressurizeable fluid source 105 described above. The spade 400 may thus be operably used in its pressurized configuration shown in FIG. 4, or may be depressurized and collapsed for insertion into, and withdrawal from, a patient.

The spade 400 may be provided with a plurality of suction ports 404 that may be connected to a vacuum source (not shown). The spade 400 may thereby employ suction to firmly grasp tissue for secure manipulation thereof. This is particularly advantageous for grasping delicate, slippery tissue without causing damage thereto. The spade 400 may additionally be provided with a central aperture 406 for providing access to tissue by other surgical instruments while the tissue is grasped by the spade 400. Although the use of suction ports 404 is described with specific reference to spade 400, it should be appreciated that suction ports may be used with any embodiment of the present invention.

Figure 5A:
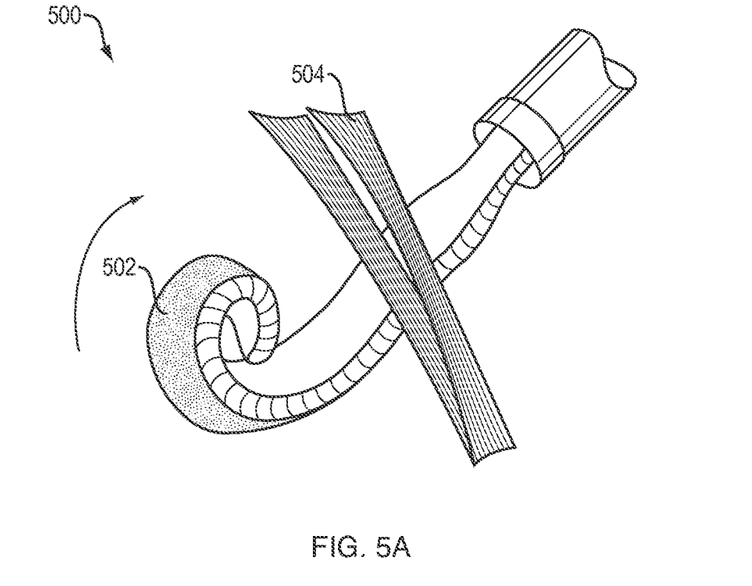
FIG. 5a is perspective view illustrating a fifth exemplary embodiment of a soft robotic instrument in accordance with the present disclosure in one of a pressurized or depressurized configuration.
Figure 5B:
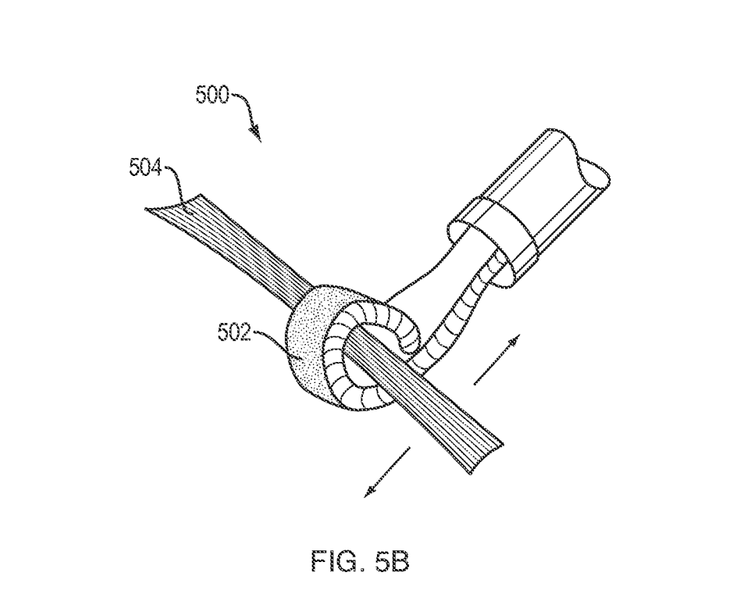
FIG. 5b is perspective view illustrating the soft robotic instrument shown in FIG. 5a in a depressurized or pressurized configuration, depending upon whether the configuration of FIG. 5a is pressurized or depressurized, respectively.

Referring to FIGS. 5a and 5b, another soft robotic laparoscopic instrument in accordance with the present disclosure may be embodied by a finger 500 that may be used to grasp tissue within a patient. The finger 500 may include a single actuator 502 that may have an internal fluid compartment that is connected to a pressurizeable fluid source (not shown) that is similar to the pressurizeable fluid source 105 described above. The finger 500 may be inserted into a patient in a depressurized, substantially straight or partially curled configuration as shown in FIG. 5a. After the finger 500 is positioned adjacent a piece of tissue 504 that is to be grasped, the actuator 502 may be pressurized, causing the finger 500 to curl or wrap around the tissue 504 one or more times as shown in FIG. 5b. The finger 500 may then be used to manipulate the tissue 504 in a desired manner. It should be appreciated that the finger 500 may be used for a variety of surgical applications, such as, for example clamping of blood vessels to provide hemostasis, applying pressure to other bodily lumens to prevent or minimize flow of fluids or gases therethrough, or to facilitate anastomosis procedures.

In addition to the various embodiments, configurations, and features described above, it is contemplated that a soft robotic laparoscopic instrument in accordance with the present disclosure may be provided with a modular configuration that would allow a plurality of different instruments (i.e., end effectors) to be interchangeably connected to a single shaft and to corresponding pressurizeable fluid sources, rigid wires, vacuum sources, etc. It is further contemplated that such a soft robotic laparoscopic instrument could be used as a manual hand instrument. It is further contemplated that such a soft robotic laparoscopic instrument could be attached to a rigid robotic arm. It is further contemplated that such a soft robotic laparoscopic instrument could be attached to a soft or hard "tentacle" of differing form factors to enable a wristed motion and control of the instrument. It is further contemplated that such a soft robotic laparoscopic instrument could be implemented in conjunction with other hard and/or soft robotic devices. It is further contemplated that such a soft robotic laparoscopic instrument could be used in open surgery as well as in minimally invasive and laparoscopic surgery.

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

While the present invention has been disclosed with reference to certain embodiments, numerous modifications, alterations and changes to the described embodiments are possible without departing from the sphere and scope of the present invention, as defined in the appended claim(s). Accordingly, it is intended that the present invention not be limited to the described embodiments, but that it has the full scope defined by the language of the following claims, and equivalents thereof.

The invention claimed is:

1. A medical device, comprising:
   an actuator, comprising a flexible molded body portion formed of an elastomeric material, a plurality of interconnected fluid compartments embedded within the elastomeric material, and a strain limiting portion disposed opposite the flexible molded body portion, wherein the actuator is moveable between a first configuration characterized by a first internal pressure within the plurality of fluid compartments and a second configuration characterized by a second internal pressure within the plurality of fluid compartments, the second internal pressure being different than the first internal pressure, and wherein the flexible molded body portion is relatively elastic compared to the strain limiting portion to cause the actuator to bend about the strain limiting portion due to an increased elasticity of the flexible molded body portion relative to the strain limiting portion when moved between the first and second configurations; and
   a fluid conduit sized and shaped to couple to a fluid source, the fluid conduit in fluid communication with at least one of the fluid compartments and adapted to transmit fluid pressure between the fluid source and the at least one fluid compartment.

2. The medical device of claim 1, wherein the first configuration is characterized by a first outer diameter and the second configuration is characterized by a second outer diameter greater than the first outer diameter.

3. The medical device of claim 2, wherein (a) the device is sized and shaped to be inserted through a structure selected from the group consisting of a dilator, an introducer sheath, a working channel of a laparoscope and a working channel of an endoscope, and (b) the first outer diameter is less than an inner diameter of the structure through which the device is sized and shaped to be inserted.

4. The medical device of claim 1, wherein the actuator, when moved from the first to the second configuration, undergoes a motion selected from the group consisting of bending, twisting, curling and straightening.

5. The medical device of claim 1, further comprising a plurality of actuators defining a grasping structure, wherein the grasping structure is open when the actuators are in a first configuration and the grasping structure is closed when the actuators are in a second configuration.

6. The medical device of claim 5, wherein the grasping structure includes a mesh, a membrane or a polymer sheet extending between the plurality of actuators, thereby defining a cup.

7. The medical device of claim 1, comprising first and second loop-shaped actuators, the second actuator being attached to, and oriented transversely relative to, the first actuator, the first and second actuators thereby defining a substantially spherical space.

8. The medical device of claim 1, further comprising a user-activated mechanism for moving fluid between the fluid source and the plurality of fluid compartments.

9. A medical device comprising:
   an actuator, comprising a flexible molded body portion formed of an elastomeric material, a plurality of interconnected fluid compartments embedded within the elastomeric material, and a strain limiting portion disposed opposite the flexible molded body portion, wherein the actuator is moveable between a first configuration characterized by a first internal pressure within the plurality of fluid compartments and a second configuration characterized by a second internal pressure within the plurality of fluid compartments, the second internal pressure being different than the first internal pressure, and the flexible molded body portion is relatively elastic compared to the strain limiting portion to cause the actuator to bend about the strain limiting portion due to an increased elasticity of the flexible molded body portion relative to the strain limiting portion when moved between the first and second configurations;
   a fluid conduit in fluid communication with at least one of the fluid compartments;
   a fluid source configured to couple to the fluid conduit; and
   a mechanism for moving fluid between the fluid source and the plurality of fluid compartments, thereby changing the configuration of the actuator.

10. The device of claim 9, further comprising a hollow shaft, wherein the actuator is slidably disposed within the hollow shaft.

11. The device of claim 10, comprising a plurality of actuators defining a grasping structure, wherein the grasping structure is open when the actuators are in a first configuration and the grasping structure is closed when the actuators are in a second configuration.

12. The device of claim 11, wherein each of the plurality of actuators includes a respective strain limiting portion, wherein the actuators bend about the strain limiting portions when moved from the first configuration to the second configuration.

13. The device of claim 11, wherein the grasping structure includes a mesh, a membrane or a polymer sheet extending between the plurality of actuators, thereby defining a cup.

14. The device of claim 9, comprising first and second loop-shaped actuators, the second actuator being attached to, and oriented transversely relative to, the first actuator, the first and second actuators thereby defining a substantially spherical space.

15. A method of comprising:
   inserting, into a body of a patient, a medical device comprising:
      an actuator, comprising a flexible molded body portion formed of an elastomeric material, a strain limiting portion disposed opposite the flexible molded body portion, and a plurality of interconnected fluid compartments embedded within the elastomeric material, wherein the actuator is moveable between a first configuration characterized by a first internal pressure within the plurality of fluid compartments and a second configuration characterized by a second internal pressure within the plurality of fluid compartments, the second internal pressure being different than the first internal pressure, and wherein the flexible molded body portion is relatively elastic compared to the strain limiting portion to cause the actuator to bend about the strain limiting portion due to an increased elasticity of the flexible molded body portion relative to the strain limiting portion when moved between the first and second configurations; and a fluid source coupled to at least one of the fluid compartments and configured to pressurize and depressurize the at least one the fluid compartments.

16. The method of claim 15, further comprising moving the actuator from the first configuration to the second configuration.

17. The method of claim 16, wherein moving the actuator from the first configuration to the second configuration includes contacting at least one of a body tissue and a medical instrument with the actuator.

18. The method of claim 16, wherein moving the actuator from the first configuration to the second configuration includes at least one of pushing, pulling or grasping a body tissue without damaging the body tissue.

19. The method of claim 15, wherein inserting the medical device into the body of the patient includes disposing a distal end of a hollow shaft within the body of the patient and advancing at least part of the medical device through the hollow shaft and into the body of the patient.

* * * * *